United States Patent [19]

Shimbara

[11] Patent Number: 5,625,197
[45] Date of Patent: Apr. 29, 1997

[54] METHOD OF DETERMINING A SCANNING INTERVAL IN SURFACE INSPECTION

[76] Inventor: Yoshimi Shimbara, 4-30, Kusatsu Higashi 2-chome, Nishi-ku, Hiroshima-shi, Hiroshima-ken, Japan

[21] Appl. No.: 322,508

[22] Filed: Oct. 17, 1994

[30] Foreign Application Priority Data

Oct. 15, 1993 [JP] Japan ..................... 5-258238

[51] Int. Cl.$^6$ .................................. G01N 21/86
[52] U.S. Cl. .................. 250/559.22; 250/559.48; 348/125; 382/286; 356/431
[58] Field of Search .............. 250/559.45, 559.46, 250/559.48, 559.22, 559.33; 348/125; 382/8, 16, 25, 27, 43, 45, 51, 54, 60, 169–172, 306, 310, 316, 286; 364/552, 553, 805, 806; 356/376, 430, 431

[56] References Cited

U.S. PATENT DOCUMENTS

| 5,319,567 | 6/1994 | Ebenstein | .................................. 382/8 |
| 5,331,408 | 7/1994 | Jordan et al. | .......................... 356/429 |

FOREIGN PATENT DOCUMENTS 62-233710  10/1987  Japan .

*Primary Examiner*—Que T. Le

[57] ABSTRACT

A scanning interval, at which an area illumination scans a subject surface for surface defect inspection, is determined based on a smallest histogram of histograms for a same value of picture elements of a two-valued image extracted in connection with all positions in a direction perpendicular to a scanning direction.

26 Claims, 8 Drawing Sheets

METHOD OF DETERMINING A SCANNING INTERVAL IN SURFACE INSPECTION

BACKGROUND OF THE INVENTION

1. Field of the Invention

The present invention relates to a method of determining a timing at which an image of an illuminated surface area is read in for image processing during surface defect inspection.

2. Description of Related Art

In typical automobile manufacturing lines including painting lines, a paint film defect inspection station, at which scratches, projections, cracks, dimples, smears and the like are detected, is located at the end of, or otherwise after, the painting line. A painted vehicle body is transferred by means of, for instance, a chain conveyor at a specified speed to the paint film defect inspection station. An image processing type of surface inspection device is used in the paint film defect inspection station to detect paint film defects. For a detailed description of a representative example of such an "image processing type" of surface inspection device, reference may be had to, for instance, Japanese Unexamined Patent Publication No. 62-233710. With the image processing type surface inspection device described in the above-mentioned publication, a specified area of illumination scans the surface of a vehicle body and an image pick-up device provides images of each scanned area.

Because scanning the surface of a vehicle body with an area illumination divides the surface into a plurality of surface areas according to scanning intervals, the entire surface is imaged by picking up images, one after another, at a timing determined based on the scanning interval. As shown in FIGS. 11A and 11B, a monochromatic image of a surface area is transformed into two-valued image. In the two-valued image, an illuminated surface area appears as a strip image expressed by a single group of bright picture elements in a dark background. Histograms of bright picture elements are produced for each X coordinate which is perpendicular to an image scanning direction Y. A histogram larger than a predetermined threshold value is detected as a scanning interval. The timing of image reading is determined based on the scanning interval.

Even though a specified area of illumination is given, if changes in an incident angle, at which light strikes a subject surface of inspection, are caused, then the width of an illuminated area changes. Such a change occurs due to unevenness of a subject surface. In such a case, the interval of image reading changes according to unevenness of the subject surface. For instance, the interval of image reading is smaller for a surface area containing a difference in level than for an even surface area. For this reason, the prior art surface inspection, in which the image reading interval is determined based only on a scanning interval, causes omissions of inspection between adjacent illumination areas.

SUMMARY OF THE INVENTION

It is an object of the present invention to provide a method of determining a scanning interval at which a subject surface is scanned by an area illumination and based on which an image of an illuminated surface area is read without any omission of image reading over a subject surface. Picture elements of an image picked up by an image pick-up device moving along with the area illumination are transformed into two-valued image data from multi-valued image data and represented by rectangular coordinates in which an X-axis is taken in a direction perpendicular to the scanning direction in which the Y-axis is taken. A histogram of picture elements between two points transitional from one value to another value and vice versa is obtained in connection with each X co-ordinate. Otherwise, a histogram may be obtained directly from adjacent picture elements having either value in connection with each X coordinate. After finding the smallest histogram among the histograms for all X co-ordinates, a scanning interval at which the area illumination scans another area of the subject surface is determined based on the smallest histogram.

If a subject surface contains uneven areas, then an image of such an uneven area is represented by a single group of picture elements having either value of the two-valued data. Histograms of these picture elements having the one value are not always the same in a transverse direction perpendicular to the scanning direction and depend upon a configuration of the uneven area. However, when the area illumination scans the subject surface at an interval corresponding to the smallest histogram among the histograms for all positions in the transverse direction and an image of the illuminated area is read at a timing determined based on the scanning interval, any omission of inspection, which is possibly caused on such an uneven area of the subject surface, is prevented from occurring.

BRIEF DESCRIPTION OF THE DRAWINGS

The above and other objects and features of the present invention will be clearly understood from the following description with respect to preferred embodiments thereof when considered in conjunction with the accompanying drawings, in which.

DETAILED DESCRIPTION OF THE PREFERRED EMBODIMENTS

Figure 1:
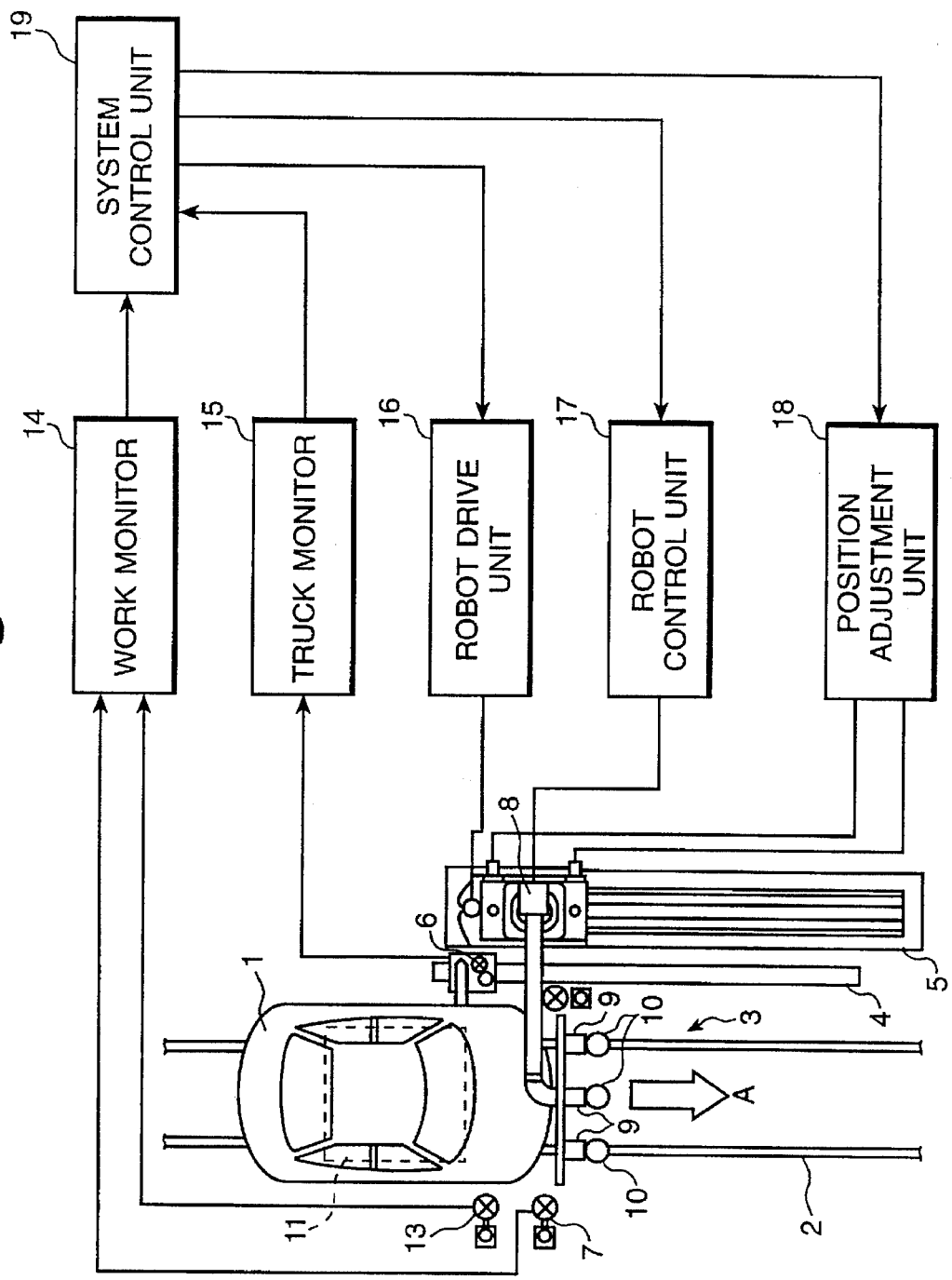
FIG. 1 is a surface inspection system in which a method of detecting an image pick-up area of the present invention is utilized.

Referring now to the drawings in detail and, in particular, to FIG. 1, which illustrates a surface inspection system used in a vehicle manufacturing line for inspection of, for instance, paint film defects of painted vehicle bodies, in which an image area detection method in accordance with a preferred embodiment of the present invention is utilized, a painted vehicle body 1 is placed on a truck 11 moving at a specified speed on parallel track rails 2 in a lengthwise direction of transportation A toward an inspection station 3. Along the track rails 2 in this inspection station 3, there are disposed work sensors 7 and 13. The work sensor 7, which may be a photoelectric tube, detects when the vehicle body 1 is placed in a specific reference position in the inspection station 3. The work sensor 13, which may be a probe sensor or an ultrasonic sensor, detects a transverse distance of the vehicle body 1 therefrom (which is hereafter referred to as a transverse deviation). On one side of and in parallel with the track rails 2 there are a synchronous truck transportation system 4 and an inspection robot drive system 5.

The synchronous truck transportation system 4 includes a contact type of truck sensor 6 which contacts the truck 11 directly and follows it up so as to detect the moved distance of the truck 11 from a specified position. Specifically, this truck sensor 6 is brought into contact with the truck 11 when the forward end of the vehicle body 1 is detected by the work sensor 7 and starts to move together with the truck 11 so as to detect the moved distance of the truck 11 from the reference position wherein the work sensor 7 is located. This sensor 7 may be of any type well known to those skilled in the art.

The inspection robot drive system 5 drives an inspection robot 8 in a direction parallel with the track rails 2. This inspection robot 8 is provided with a plurality of, for instance three in this embodiment but not limited to three, cameras or image pick-up devices 9 capable of picking up images of the vehicle body 1 from above and the same number of, i.e. three, marking devices 10 for marking detected paint film defects. These image pick-up devices are arranged at regular intervals in the transverse direction perpendicular to the track rails 2. Similarly, these markers 10 are arranged at the same regular intervals in the transverse direction. In the case where three image pick-up devices 9 are provided, they provide images of three sections into which the top surface of the vehicle body 1 is spatially divided in the transverse direction. Images provided by these image pick-up devices 9 are sent timely to and processed in an image processing unit 12 including a microcomputer which will be described later.

The surface inspection system further includes a work monitor unit 14, a truck monitor unit 15, a synchronous robot drive unit 16, an inspection robot control unit 17, a transverse position adjustment unit 18, and an inspection system control unit 19. The work monitor unit 14 receives signals from the work sensors 7 and 13 and puts out a signal indicative of arrival of the vehicle body 1 at the specified reference position in the inspection station 3 and a signal representing a transverse deviation of the vehicle body 1. The truck monitor unit 15 receives a signal, representing a distance that the truck 11 has moved from the reference position, from the truck sensor 6 and puts out a signal indicative of a position of the vehicle body 1 on the basis of the moved distance of the truck 11. The inspection system control unit 19 receives these signals from the work monitor unit 14 and the truck monitor unit 15 and, based on these signals, calculates the position of the vehicle body 1 relative to the truck 11 with the use of a signal from the work sensor 7 as a trigger signal and provides for the synchronous robot drive unit 16, the inspection robot control unit 17 and the transverse position adjustment unit 18 control signals. The synchronous robot drive control unit 16 causes the robot drive system 5 to control movement of the inspection robot 8, such as timing, direction and speed, based on the control signal from the system control unit 19. The robot control unit 17 controls, based on the control signal from the system control unit 19, the image pick-up devices 9 and the markers 10 in operation. The transverse position adjustment unit 18 is caused to control the inspection robot 8 based on the control signal from the system control unit 19 so as to adjust the image pick-up devices 9 and the markers 10 in transverse position and direction.

Figure 2:
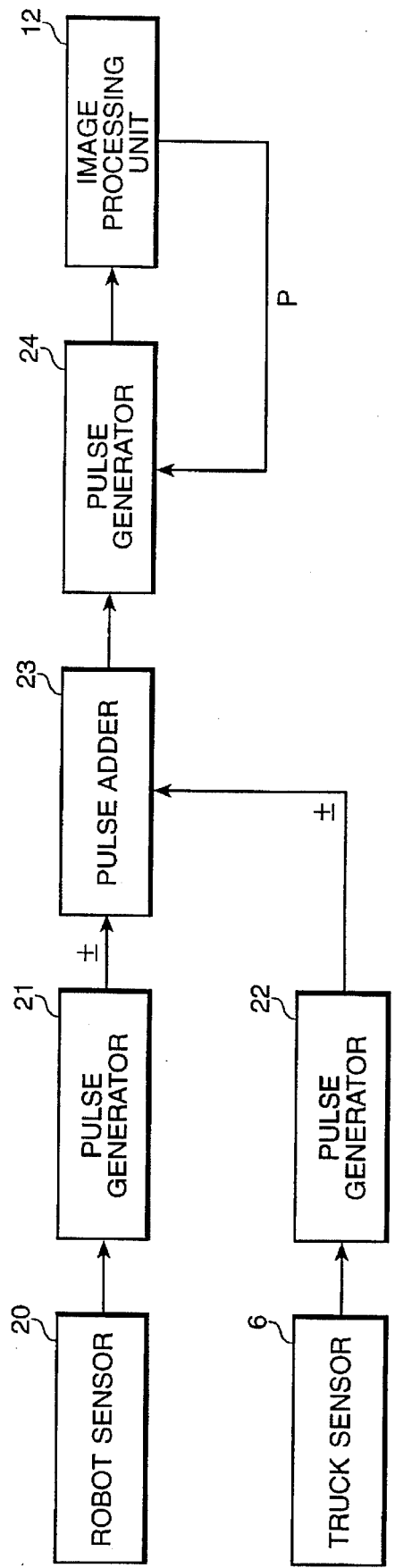
FIG. 2 is a block diagram showing a timing control of image reading during surface inspection.
Figure 3A:
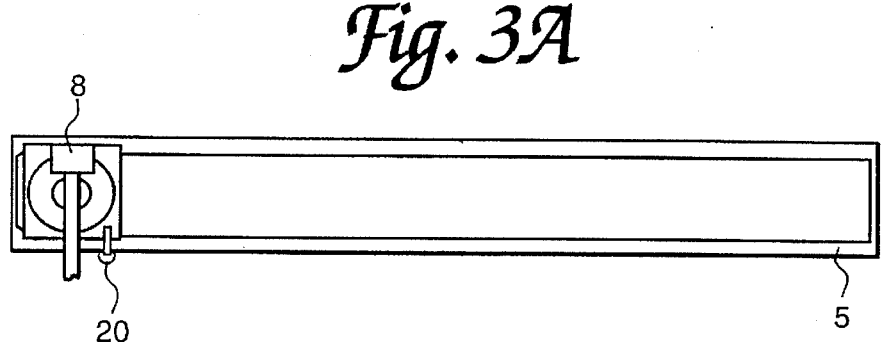
FIG. 3A is a plan view schematically showing an inspection robot drive system.
Figure 3B:
FIG. 3B is a schematic illustration showing a pulse train representing a distance of movement of an inspection robot.

FIG. 2 shows an image read-in timing control system for controlling a timing at which the image processing unit 12 reads in image signals from the image pick-up devices 9. The control system includes a robot sensor 20, which is provided as an integral part of the inspection robot 8 (see FIG. 3A), for detecting a moved distance of the inspection robot 8. A signal, indicative of the moved distance of the inspection robot 8 from the robot sensor 20, causes a pulse generator 21 to generate pulses (see FIG. 3B) at regular intervals. The number of pulses is proportional to the distance of movement of the inspection robot 8. On the other hand, a signal from the truck sensor 6, indicative of the moved distance of the truck 11, causes a pulse generator 22 to generate pulses (see FIG. 3D) at regular intervals. The number of pulses is proportional to the distance moved by the truck 11. These distance pulses are added together in a pulse adder 23 and then sent as composed distance pulses to a pulse generator 24. As was previously described, since the signal from the truck sensor 6 represents a moved distance of the vehicle body 1 placed on the truck 11, the composed distance pulse represents a relative position in the lengthwise direction of transportation A between the vehicle body 1 and the image pick-up devices 9. The pulse generator 24 generates an image read-in pulse (see FIG. 3E) at a time determined based on the composed distance pulse and a signal representative of scanning interval P, detected in the image processing unit 12 as will be described later. When the image read-in pulse is provided, the image processing unit 12 reads in image signals of an image picked up by the image pick-up devices 9 and then performs necessary image processing, such as transforming multi-valued image data into two-valued image data, so as to provide a black-and-white image.

Figure 3C:
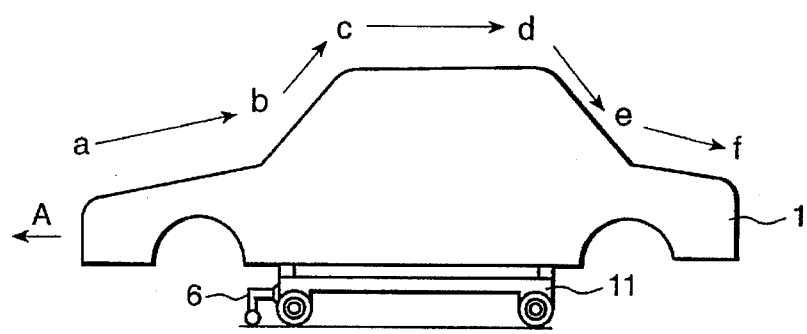
FIG. 3C is a schematic illustration showing a route of movement of the inspection robot.
Figure 3D:
FIG. 3D is a schematic illustration showing a pulse train representing a distance of movement of a transportation truck.
Figure 3E:
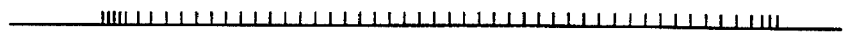
FIG. 3E is a schematic illustration showing a pulse train for controlling image reading.

As shown in FIG. 3C, the inspection robot 8 moves, taking a programmed route a to f in alphabetical order, over the vehicle body 1.

In the vehicle manufacturing line, when a painted vehicle body 1 placed on the truck 11 is transported to the inspection station 3, the work monitor unit 14 puts out a signal representing a transverse deviation of the vehicle body 1 from the work sensor 13 and, according to this signal, the position adjustment unit 18 controls the inspection robot 8 for adjustment of the image pick-up devices 9 and the markers 10 in transverse position and viewing direction. Subsequently, when the work sensor 7 detects the painted vehicle body 1 and provides a signal, the truck sensor 6 is brought into contact with the truck 11 and, thereafter, moves together with the truck 11 as one whole so as to detect a moved distance of the truck 11. Simultaneously, the image pick-up devices 9 start to pick up images of the surface of the painted vehicle body 1. In order to pick up images with the image pick-up devices 9, a surface light source (not shown) provides a fixed area of illumination incident upon the surface of the vehicle body 1 at a specified incident angle so as to illuminate at least a part of, desirably the whole section of, the body surface covered within the field of view of each image pick-up device 9. The area illumination has a lengthwise width similar to the lengthwise width of the field of view of the image pick-up device 9 and extends transversely across over the width of the vehicle body 1.

Since the vehicle body 1 is transported at a constant speed in the lengthwise direction of transportation A, the area illumination scans over the entire surface of the vehicle body 1 from the front end to the rear end. During image-picking up, the inspection robot 8 may be moved in a direction opposite to the lengthwise direction of transportation A.

Because the speed at which the area illumination moves on the surface of vehicle body 1 in the lengthwise direction of transportation A is found from the relative position between the moving vehicle body 1 and the image pick-up devices 9, the interval of generation of image read-in control pulse signals, which are generated based on a composed distance pulse which represents the relative position between the moving vehicle body 1 and the image pick-up devices 9, indicates an interval at which the image processing unit 12 reads in images according to a moved distance of the area illumination. In other words, the entire surface of the vehicle body 1 is spatially divided into a plurality of lengthwise sections having a lengthwise width corresponding to the interval, and images of these sections picked up by the image pick-up devices 9 are read in the image processing unit 12 at the intervals. One transverse row of images after another transverse row of images is read.

Figure 5:
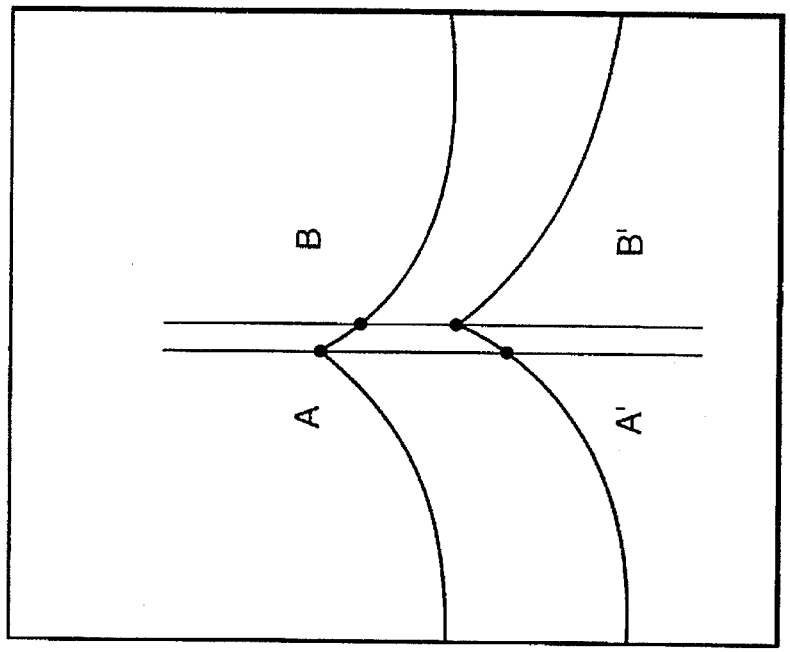
FIG. 5 is an illustration showing a histogram in the Y-direction of the image.

In this instance, even when the area of illumination is directed to the surface of the vehicle body 1 at a specified angle, if there are uneven portions and/or inclined portions in the surface of the vehicle body 1, then angles at which light rays strike are different between even surface portions and irregular or uneven surface portions. Consequently, the quantity of reflected light is different at the image pick-up device 9 between the even surface portions and the uneven surface portions. As an example, inspecting a generally even surface containing uneven surface portions, such as a bonnet or engine hood with an inclined difference in level in the lengthwise direction Y and extending in the transverse direction X, the two-valued image 25 is read in from the image pick-up device 9, which contains a bright strip image 26 in a dark background such as shown in FIG. 5. Specifically, the bright strip image 26 changes in shape according to configurations of differences. The smallest width W1 of the bright strip image 26 represents the steepest portion of the difference. If the area illumination moves a lengthwise distance longer than the smallest width W1 of the bright strip image 26 after the image processing unit 12 has read in the image 25 and then reading-in of another image of an illuminated portion of the surface of the vehicle body 1 takes place, then an omission in inspection on a surface portion successive to the difference occurs. Accordingly, the image read-in control pulse signal must be such that it causes the image processing unit 12 to read in another image when the area illumination has moved less than the smallest width W1 of the bright strip image 26 in the last image 25 read therein. In order to avoid such an omission, the smallest width of the bright strip image 26 in the image 25 is detected as a scanning interval P at which the area illumination is moved for another image pick-up.

The detection of scanning interval P described above will be best understood by reviewing FIG. 6, which is a flow chart illustrating a sequence routine of scanning interval detection for the microcomputer of the image processing unit 12. Programming a computer is a skill well understood in the art. The following description is written to enable a programmer having ordinary skill in the art to prepare an appropriate program for the microcomputer. The particular details of any such program would of course depend upon the architecture of the particular computer selected.

Figure 4:
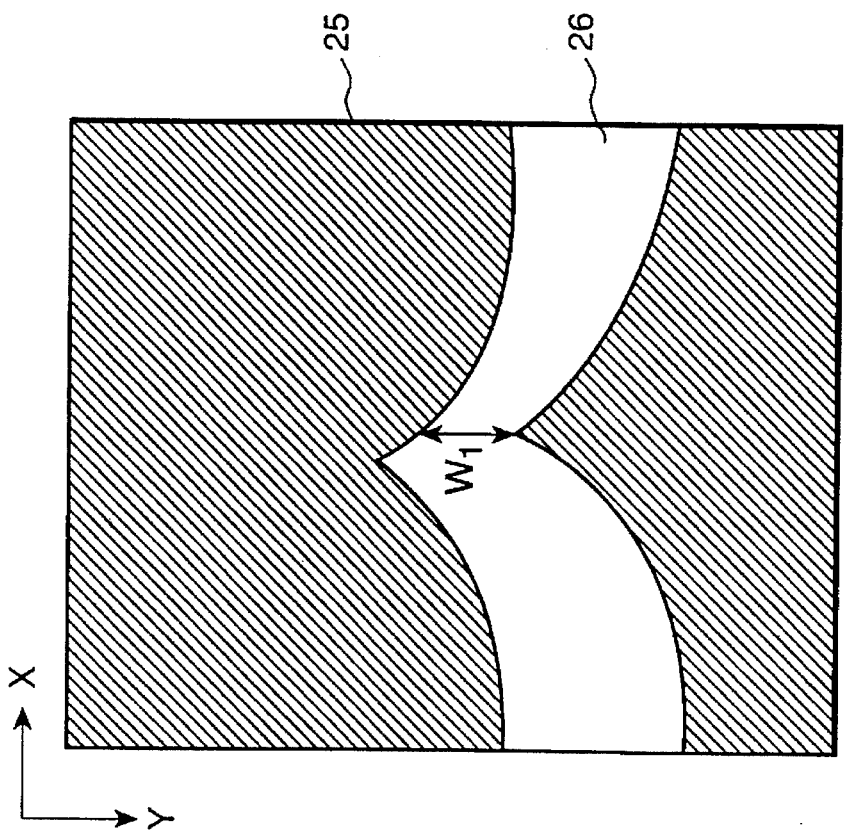
FIG. 4 is an illustration showing an image provided by an image pick-up device.
Figure 6:
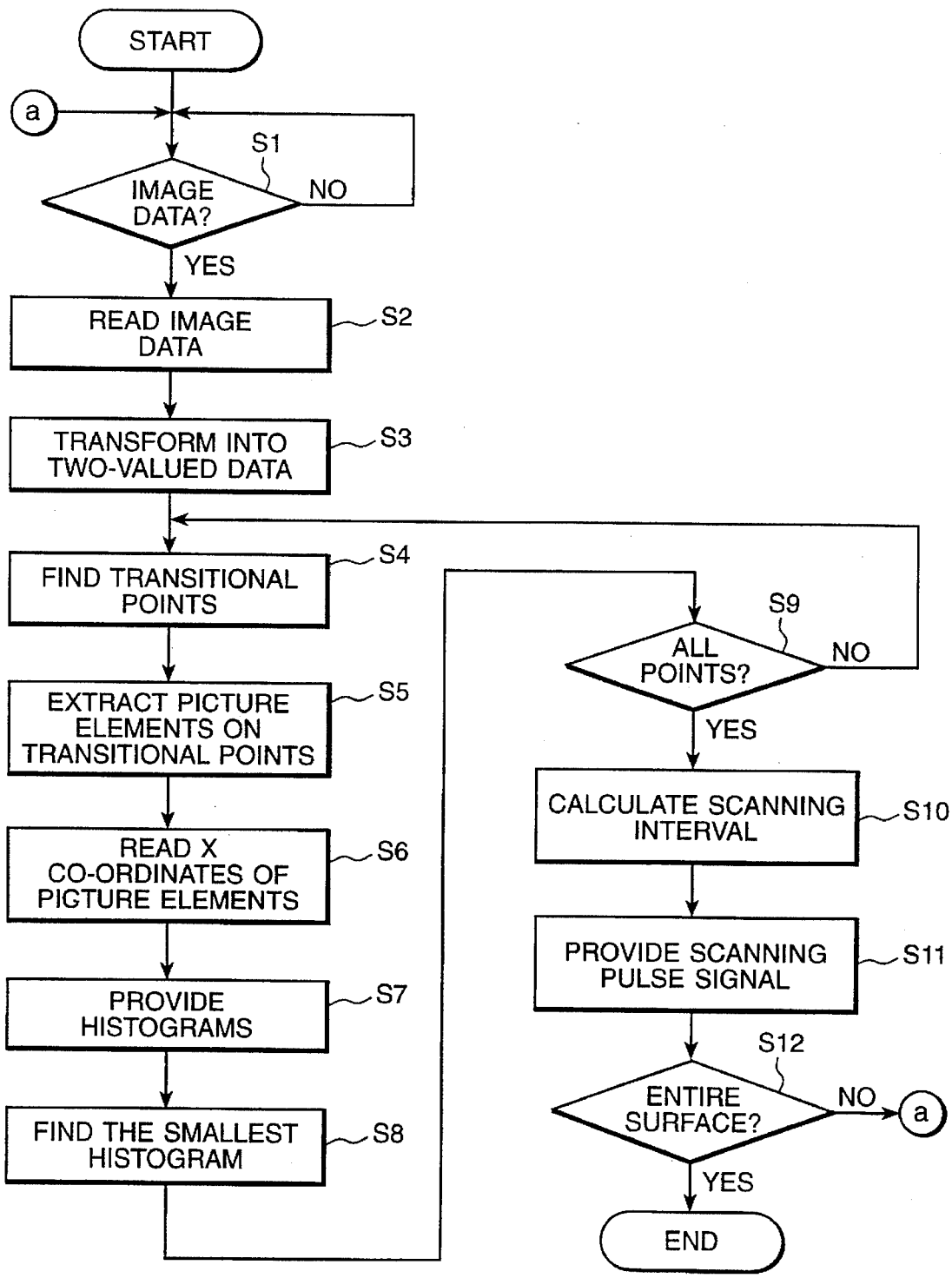
FIG. 6 is a flow chart illustrating a sequence routine of a detection of an image pick-up area in accordance with a preferred embodiment of the present invention.

FIG. 6 is a flow chart illustrating the scanning interval detection sequential routine. The first step S1 is to make a decision as to whether the image pick-up devices 9 provide image data upon the occurrence of an image read-in pulse signal. This decision is repeatedly made at step 1 until image data is provided. When data representative of an image 25 is provided, after the image processing unit 12 has read in the image data at step S2, it transforms the data from multi-valued image data into two-valued image data at step S3 so as to discriminate a difference expressed as a bright strip image 26 by bright picture elements from the even surface portion expressed as a dark background in the image 25 by dark picture elements. These bright and dark picture elements of the image 25 are represented in position by rectangular co-ordinates, as shown in FIG. 4, where the X-axis is taken in the transverse direction in which the difference extends and the Y-axis is taken in the lengthwise direction in which the area illumination scans the vehicle body surface.

Thereafter, the image processing unit 12 scans the monochromatic image 25 in the Y-direction so as to find transitional points from dark to bright and transitional points from bright to dark at step S4 and extract all bright picture elements existing on the transitional points at step S5. As a result, the bright strip image 26 is figured out as a region defined between the two rows of bright picture elements. In other words, there are two bright picture elements having the same X co-ordinate, i.e., one on the first row of bright picture elements and another on the second row of bright picture elements. Then, after retrieving X coordinates of the bright picture elements on the transitional points at step S6, a calculation is made at step S7 so as to find a Y coordinate distance between each of the two bright picture elements having the same X coordinate. Because this distance represents the number of bright picture elements, i.e. a histogram H relating to bright picture elements, having the same X coordinate can be generated. The histograms H for all X co-ordinates can be said that they express a change in the lengthwise width of the bright strip image 26 in the Y direction.

Subsequently, the smallest histogram $H_{min}$ is found among the histograms H at step S8. For example, a comparison is made to determine which is smaller between a histogram H(AA') for an X co-ordinate which is represented by a distance between two transitional points A and A' and a histogram H(BB') for another X co-ordinate which is represented by a distance between two transitional points B and B' as shown in FIG. 5. In such a manner, all of the histograms H are compared to one another so as to extract, for instance, the histogram H(BB') as the smallest histogram $H_{min}$. At step S9, a decision is made as to whether all of transitional points have been extracted. If not, then histograms regarding bright picture elements at the remaining transitional points are prepared and compared in order to find the smallest histogram through steps S4 to S8. Then, at step S10, the actual distance on the vehicle body surface corresponding to the minimum width of the bright strip image 26 is calculated as a scanning interval P based on the smallest histogram $H_{min}$. The scanning interval P is expressed by the following equation:

$$P=H_{min} \times SF$$

In this equation, SF is a coefficient (mm/picture element) of scanning interval conversion for a single picture element.

At step S11, the image processing unit 12 provides, for the pulse generator 24, a pulse representing the scanning interval P. As a result, as was previously described, the pulse generator 24 generates an image read-in pulse signal for reading of another image based on the composed distance pulse and the pulse of scanning interval P. That is, immediately before the area illumination has moved through the scanning interval P, the image processing unit 12 starts to read in another bright strip image 26. The timing of image reading is determined in this manner and another surface section is defined by the area illumination for continuous surface inspection. The determination of image reading timing is repeatedly executed until the area illumination scans over the entire surface of the vehicle body 1. When scanning of the entire surface of the vehicle body 1 is completed at step S12, the sequence routine goes to end.

Figure 7:
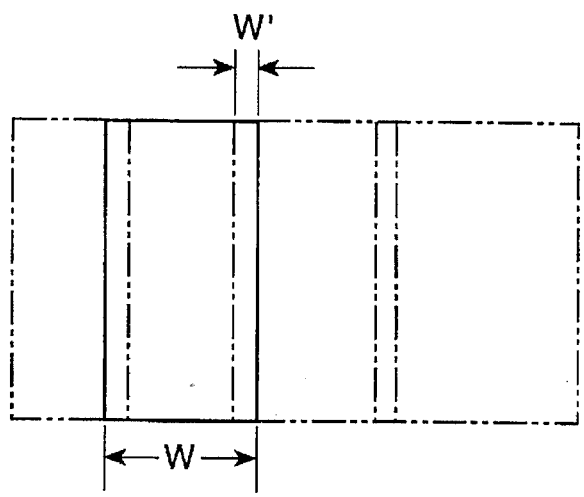
FIG. 7 is an illustration showing an image read-in width.

Since the interval of scanning with the area illumination is no greater than the smallest lengthwise width of a bright strip image, omission of inspection does not occur even though the lengthwise width of a bright strip image changes in the transverse direction. Further, because the image processing unit 12 starts to read a bright strip image before the area illumination has moved a scanning interval P determined according to the preceding bright strip image, there is provided an overlapped margin W' in the lengthwise direction between two adjacent scanned sections as shown in FIG. 7. Consequently, omission of surface inspection is not caused over the surface of the vehicle body 1 even if there may occur control errors.

Figure 8:
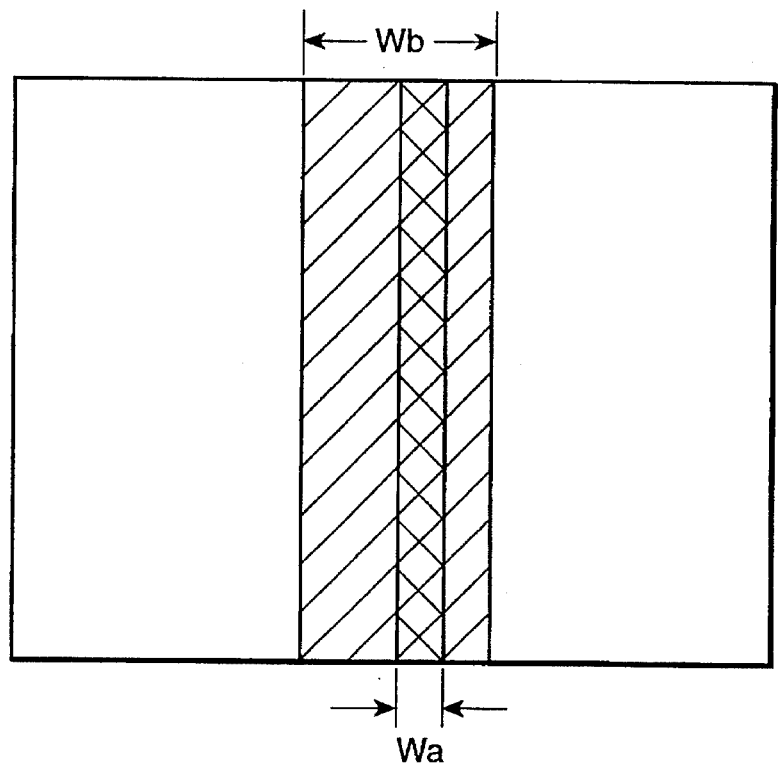
FIG. 8 is an illustration showing a relationship between image read-in widths for a flat inspection surface and a curved inspection surface.

Changes in the widths of strip images are caused not only due to such a surface difference in level but also due to curved surface portions, such as front and rear end portions of the vehicle body 1. Accordingly, the bright strip image changes in lengthwise width to a width Wa for the curved surface portion which is narrow as compared to a width Wb for an even surface, as shown in FIG. 8. The scanning interval P for such a considerably narrow bright strip image may, of course, be calculated in the manner as described above, or otherwise calculated in another manner if the surface portion does not contain any differences in transverse direction.

Paint film defects in the vehicle body surface, such as scratches, projections, cracks, dimples, smears and/or the like, and positions of these paint film defects are detected as signal irregularities contained in two-valued image data representative of each image. According to the positions of these paint film defects, the system control unit 19 causes the robot control unit 17 to shift the inspection robot 8 so as to place the markers 10 in the positions for marking. The vehicle body 1, inspected and marked, is continuously transported to a polishing station (not shown) for polishing and finishing the marked paint film defects in any manner well known to those skilled in the art.

Figure 9:
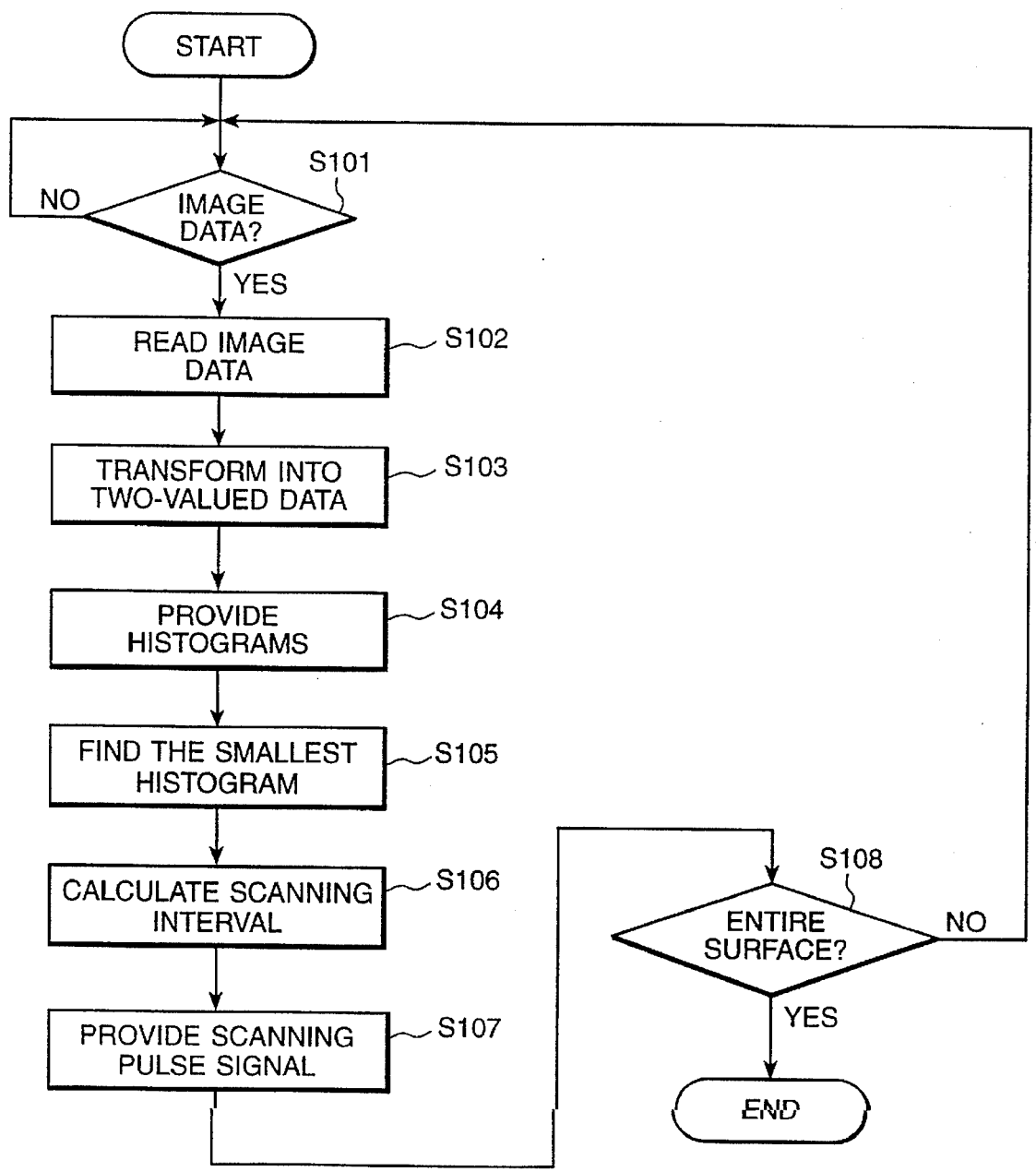
FIG. 9 is a flow chart illustrating a sequence of a detection of an image pick-up area in accordance with another preferred embodiment of the present invention.
Figure 10:
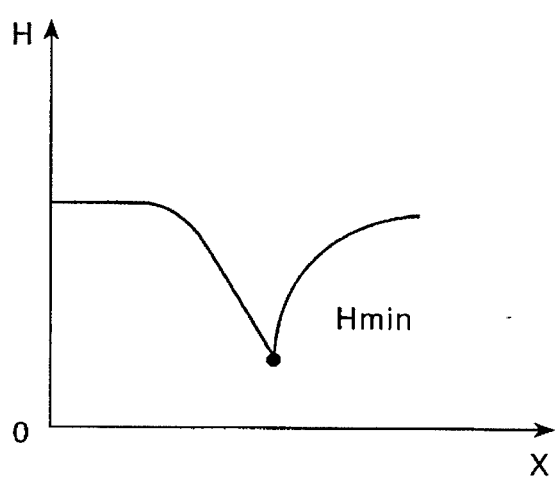
FIG. 10 is an illustration showing a histogram in a Y-direction of an image having a pick-up area which is detected by way of the sequence illustrated in FIG. 9.
Figure 11A:
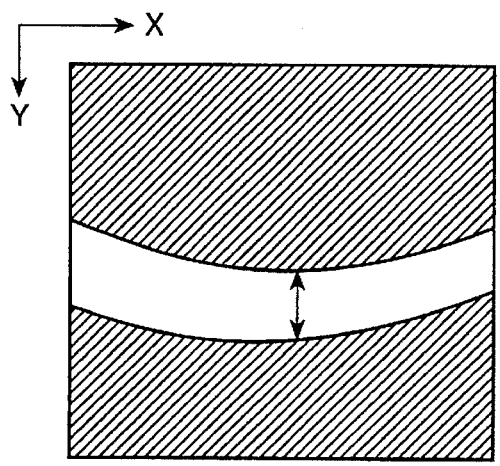
FIG. 11A is an illustration showing an image whose image pick-up area is detected by way of a prior art method.
Figure 11B:
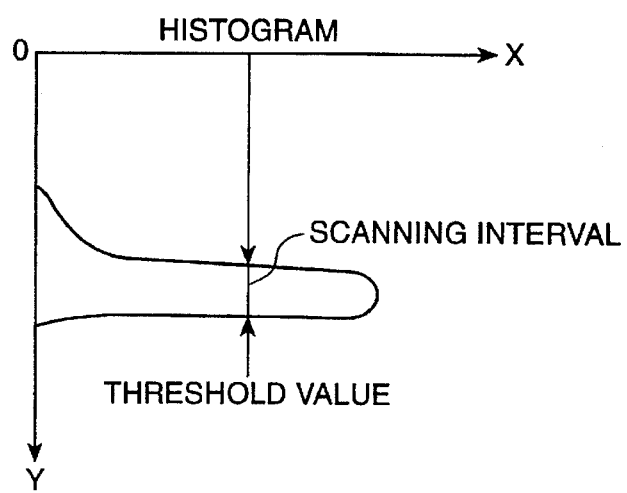
FIG. 11B is an illustration showing a histogram in the Y-direction of the image shown in FIG. 11A.

The scanning interval may be detected in another way having a sequence routine which is illustrated by a flow chart shown in FIG. 9.

Referring to FIG. 9, after having made a decision at step S101 as to whether there is image data upon the occurrence of an image read-in signal, the image processing unit 12 reads in the image data as multi-valued image data at step S102 and then transforms the image data from multi-valued data into two-valued data at step S103 so that the bright strip image 26 is discriminated as a single group of bright picture elements from the dark background expressed as groups of dark picture elements in the image 25. These bright and dark picture elements of the image 25 are represented in rectangular coordinates, as was described in connection with FIG. 4.

Thereafter, the image processing unit 12 counts bright picture elements having the same X coordinate, i.e. extracts a histogram H relating to bright picture elements having the same X co-ordinate, at step S104. The histograms H for all X co-ordinates are compared to one another so as to find the smallest histogram $H_{min}$ among them at step S105. Subsequently, at step S106, the actual distance corresponding to the minimum width of strip image 26 is calculated as a scanning interval P, based on the smallest histogram $H_{min}$, from the equation, $P=H_{min} \times SF$.

At step S107, the image processing unit 12 provides, for the pulse generator 24, a pulse representing a scanning interval P for another scan. As a result, as was previously described, the pulse generator 24 generates an image read-in pulse signal for reading in another image in the same manner as described in relation to the foregoing embodiment. When the timing of image reading is determined in such a way, another surface section is defined for another surface inspection. When scanning of the entire surface of the vehicle body 1 is completed at step S12, the sequence routine goes to end.

It is to be understood that although the present invention has been described with regard to preferred embodiments thereof, various other embodiments and variants may occur to those skilled in the art which are within the scope and spirit of the invention. Such other embodiments and variants are intended to be covered by the following claims.

What is claimed is:

1. A method of determining a scanning interval, at which (1) an area illumination for illuminating a surface of a subject including surface irregularities in a transverse direction perpendicular to a scanning direction and (2) an image pick-up device for providing multi-valued data representative of an image of an illuminated area of the subject surface are moved relative to said subject surface in the scanning direction so as to scan the subject surface continually for surface defect inspection, the scanning interval determining method comprising the steps of:

transforming the multi-valued data representative of each of a plurality of picture elements of said image provided by said image pick-up device into two-valued data;

scanning said image in said transverse direction so as to extract transitional points between two of said picture elements adjacent to each other in said transverse direction which have differences in said two-valued data;

providing a histogram of picture elements, existing between two adjacent extracted transitional points in said scanning direction, with respect to said transverse direction and determining a minimum value from said histogram; and determining said scanning interval, based on said minimum value, at which said area illumination and said image pickup device are moved relative to said subject surface in said scanning direction for scanning another area of said subject surface.

2. A method of determining a scanning interval as defined in claim 1, wherein said area illumination moves in said scanning direction intermittently.

3. A method of determining a scanning interval as defined in claim 2, wherein said step of determining said scanning interval provides an overlap between adjacent illuminated areas.

4. A method of determining a scanning interval as defined in claim 1, and further comprising the step of subjecting said image to image processing before said area illumination has moved a distance according to said scanning interval.

5. A surface scanning method as defined in claim 1, wherein said subject surface is a painted surface including surface irregularities therein.

6. A surface scanning method as defined in claim 1, wherein said subject surface is a painted surface of a car body including surface irregularities therein.

7. A surface scanning method as defined in claim 3, wherein said subject surface is a painted surface including surface irregularities therein.

8. A surface scanning method as defined in claim 3, wherein said subject surface is a painted surface of a car body including surface irregularities therein.

9. A method of determining a scanning interval, at which (1) an area illumination for illuminating a surface of a subject including surface irregularities in a transverse direction perpendicular to a scanning direction and (2) an image pick-up device for providing multi-valued data representative of an image of an illuminated area of the subject surface are moved relative to said subject surface in the scanning direction so as to scan the subject surface continually for surface defect inspection, the scanning interval determining method comprising the steps of:

transforming the multi-valued data representative of each of a plurality of picture elements of said image provided by said image pick-up device into two-valued data;

scanning said two-valued data in said scanning direction so as to extract picture elements having one data value of said two-valued data;

providing histograms of picture elements, having said one data value in said scanning direction, with respect to said transverse direction and determining a minimum histogram of said histograms; and determining said scanning interval, based on said minimum histogram, at which said area illumination and said image pick-up device are moved relative to said subject surface in said scanning direction for scanning another area of said subject surface.

10. A method of determining a scanning interval as defined in claim 9, wherein said area illumination moves in said scanning direction intermittently.

11. A method of determining a scanning interval as defined in claim 10, wherein said step of determining said scanning interval provides an overlap between adjacent illuminated areas.

12. A surface scanning method as defined in claim 9, wherein said subject surface is a painted surface including surface irregularities therein.

13. A surface scanning method as defined in claim 9, wherein said subject surface is a painted surface of a car body including surface irregularities therein.

14. A surface scanning method as defined in claim 11, wherein said subject surface is a painted surface including surface irregularities therein.

15. A surface scanning method as defined in claim 11 wherein said subject surface is a painted surface of a car body including surface irregularities therein.

16. A surface scanning method for continually scanning a subject surface, including surface irregularities, in a transverse direction intersecting a scanning direction comprising the steps of:

intermittently shifting an area illumination so as to illuminate areas of the subject surface in a scanning direction;

providing an image of each of said illuminated areas at a given timing;

scanning said image so as to detect deflection of said image in said scanning direction according to surface unevenness of one of said illuminated areas; and changing said given timing for providing an image of another of said illuminated areas subsequent to said one of said illuminated areas based on said deflection of said image.

17. A surface scanning method for continually scanning a subject surface, including surface irregularities, in a transverse direction intersecting a scanning direction comprising the steps of:

intermittently shifting an area illumination so as to illuminate areas of the subject surface in a scanning direction;

providing multi-valued data representative of an image of each of said illuminated areas at a given timing;

transforming multi-valued data representative of each of a plurality of picture elements of said image into two-valued data;

scanning said image in said transverse direction so as to extract transitional points between two picture elements adjacent to each other in said transverse direction and differing in said two-valued data;

providing a histogram of picture elements, existing between adjacent transitional points in said scanning direction, with respect to said transverse direction and extracting a smallest value from said histogram; and changing said given timing for providing an image of another illuminated area adjacent to a scanned area of said subject surface based on said smallest value.

18. A surface scanning method as defined in claim 17, and further comprising the step of advancing said given timing earlier as said smallest value becomes smaller.

19. A surface scanning method as defined in claim 17, wherein said given timing is changed so as to provide an overlap between adjacent illuminated areas.

20. A surface scanning method as defined in claim 17, wherein said subject surface is a painted surface including surface irregularities therein.

21. A surface scanning method as defined in claim 17, wherein said subject surface is a painted surface of a car body including surface irregularities therein.

22. A surface scanning apparatus for continually scanning a subject surface, including surface irregularities, in a transverse direction intersecting a scanning direction comprising:

illumination means for intermittently illuminating areas of the subject surface in a scanning direction;

image pick-up means for providing multi-valued data representative of an image of each of said illuminated areas at a given timing;

data processing means for (1) transforming multi-valued data representative of each of a plurality of picture elements of said image into two-valued data, (2) scanning said image in said transverse direction so as to extract transitional points between two picture elements, adjacent to each other in said transverse direction, which differ in said two-valued data, (3) providing a histogram of picture elements, which exist between each adjacent pair of said transitional points in said scanning direction, with respect to said transverse direction, and (4) extracting the smallest value from said histogram; and timing control means for changing said given timing for providing an image of another illuminated area, adjacent to a scanned area of said subject surface, based on said smallest value.

23. A surface scanning apparatus as defined in claim 22, wherein said timing control means advances said given timing earlier as said smallest value becomes smaller.

24. A surface scanning apparatus as defined in claim 22, wherein said timing control means changes said given timing so as to provide an overlap between adjacent illuminated areas.

25. A surface scanning method as defined in claim 22, wherein said subject surface is a painted surface including surface irregularities therein.

26. A surface scanning method as defined in claim 22, wherein said subject surface is a painted surface of a car body including surface irregularities therein.

* * * * *